US00RE45266E

(19) United States
(12) Reissued Patent
Adelson

(10) Patent Number: US RE45,266 E
(45) Date of Reissued Patent: Dec. 2, 2014

(54) TACTILE SENSOR USING ELASTOMERIC IMAGING

(71) Applicant: Edward Adelson, Winchester, MA (US)

(72) Inventor: Edward Adelson, Winchester, MA (US)

(73) Assignee: Massachusetts Institute of Technology, Cambridge, MA (US)

(21) Appl. No.: 14/045,647

(22) Filed: Oct. 3, 2013

Related U.S. Patent Documents

Reissue of:

(64) Patent No.: 8,411,140
Issued: Apr. 2, 2013
Appl. No.: 12/488,008
Filed: Jun. 19, 2009

U.S. Applications:

(63) Continuation of application No. 13/971,456, filed on Aug. 20, 2013, now Pat. No. Re. 44,856, which is an application for the reissue of Pat. No. 8,411,140.

(60) Provisional application No. 61/073,904, filed on Jun. 19, 2008.

(51) Int. Cl.
*H04N 7/18* (2006.01)
*G06K 9/00* (2006.01)

(52) U.S. Cl.
USPC ..... 348/135; 382/124

(58) Field of Classification Search
USPC ..... 348/92, 135, 77; 382/124, 125, 126, 382/115, 127, 116; 396/15
See application file for complete search history.

(56) References Cited

U.S. PATENT DOCUMENTS

| | | | |
|---|---|---|---|
| 4,120,585 | A | 10/1978 | DePalma et al. |
| 4,340,300 | A | 7/1982 | Ruell |
| 4,481,815 | A | 11/1984 | Overton |
| 4,549,093 | A | 10/1985 | Severwright |

(Continued)

FOREIGN PATENT DOCUMENTS

| | | | |
|---|---|---|---|
| JP | 2005121858 | A | 5/2005 |
| JP | 2007520040 | A | 7/2007 |

(Continued)

OTHER PUBLICATIONS

Mackawa et al., "Development of a Finger-Shaped Tactile Sensor and its Evaluation by Active Touch" Proceedings of the 1992 IEEE International Conference on Robotics and Automation, Nice, France, May 1992, pp. 1327-1334.

(Continued)

*Primary Examiner* — Behrooz Senfi
(74) *Attorney, Agent, or Firm* — Gesmer Updegrove LLP

(57) ABSTRACT

A tactile sensor includes a photosensing structure, a volume of elastomer capable of transmitting an image, and a reflective skin covering the volume of elastomer. The reflective skin is illuminated through the volume of elastomer by one or more light sources, and has particles that reflect light incident on the reflective skin from within the volume of elastomer. The reflective skin is geometrically altered in response to pressure applied by an entity touching the reflective skin, the geometrical alteration causing localized changes in the surface normal of the skin and associated localized changes in the amount of light reflected from the reflective skin in the direction of the photosensing structure. The photosensing structure receives a portion of the reflected light in the form of an image, the image indicating one or more features of the entity producing the pressure.

29 Claims, 10 Drawing Sheets

NEW

(56) References Cited

U.S. PATENT DOCUMENTS

| | | | | |
|---|---|---|---|---|
| 4,584,625 | A | 4/1986 | Kellogg | |
| 4,588,348 | A | 5/1986 | Beni et al. | |
| 4,775,961 | A | 10/1988 | Capek et al. | |
| 5,357,799 | A | 10/1994 | Roth et al. | |
| 5,448,649 | A | 9/1995 | Chen et al. | |
| 5,616,839 | A | 4/1997 | Chen et al. | |
| 5,737,071 | A * | 4/1998 | Arndt | 356/71 |
| 5,967,940 | A | 10/1999 | Yamaguchi | |
| 5,967,990 | A | 10/1999 | Thierman et al. | |
| 6,144,757 | A * | 11/2000 | Fukuzumi | 382/124 |
| 6,234,031 | B1 * | 5/2001 | Suga | 73/862.474 |
| 6,909,084 | B2 | 6/2005 | Tachi et al. | |
| 7,707,001 | B2 * | 4/2010 | Obinata et al. | 702/127 |
| 2003/0178556 | A1 | 9/2003 | Tachi et al. | |
| 2004/0237669 | A1 * | 12/2004 | Hayward et al. | 73/862.624 |
| 2004/0252867 | A1 * | 12/2004 | Lan et al. | 382/124 |
| 2004/0255128 | A1 * | 12/2004 | Ohba | 713/186 |
| 2006/0119837 | A1 * | 6/2006 | Raguin et al. | 356/71 |
| 2007/0146536 | A1 | 6/2007 | Lemoine | |
| 2007/0288186 | A1 | 12/2007 | Datta et al. | |
| 2008/0106258 | A1 | 5/2008 | Torres-Jara | |
| 2008/0219521 | A1 * | 9/2008 | Benkley et al. | 382/124 |
| 2008/0284925 | A1 * | 11/2008 | Han | 349/12 |
| 2010/0284565 | A1 * | 11/2010 | Benkley et al. | 382/103 |

FOREIGN PATENT DOCUMENTS

| | | |
|---|---|---|
| JP | 2008008746 A | 1/2008 |
| WO | 2005085766 | 9/2005 |
| WO | 2006098719 | 9/2006 |

OTHER PUBLICATIONS

Lee et al., "A Modular Expandable Tactile Sensor Using Flexible Polymer" 18th IEEE International Conference 2005, pp. 642-645.

Begej, "Planar and Finger-Shaped Optical Tactile Sensors for Robotic Applications" IEEE Journal of Robotics and Automation, vol. 4, No. 5, Oct. 1988, pp. 472-484.

Hritsu et al., "The performance of a deformable-membrane tactile sensor: basic results on geometrically-defined tasks" IEEE International Conference on Robotics and Automation 2000, pp. 508-513.

Heo et al., "Tactile Sensor arrays using fiber Bragg grating sensors" Sensors and Actuators A 126, 2006 pp. 312-327.

Maheshwari et al., "Tactile Sensors to Sense Touch on a Par with a Human Finger" Angewandte Chem. Int. Ed. 2008, 47, pp. 7808-7826.

Maheshwari et al., "High-Resolution Thin Film Device to Sense Texture by Touch" Science, vol. 312, Jun. 9, 2006, pp. 1501-1504.

Full et al., "Maximum single leg force production: Cockroaches Righting on Photoelastic Gelatin" The Journal of Experimental Biology 198, 1995, pp. 2441-2452.

O'Gorman et al., "Fingerprint Verification" Chapter 2, Biometrics:Personal Identification in Networked Society 1999, 1-22.

Graz et al., "Flexible ferroelectret field-effect transistor for large-area sensor skins and microphones" Applied Physics Letters, 89, 2006, pp. 073501-1-073501-3.

NODA, "300nm-Thick Cantilever in PDMS for Tactile Sensing" 2005 IEEE pp. 283-286.

English Translation of Japanese Notice of Rejection issued on Aug. 7, 2012 in connection with Japanese Patent Appln. No. 2011-514834, 2 pages.

International Search Report and Written Opinion issued on Jan. 21, 2010 in connection with International Application PCT/US2009/047930, 11 pages.

International Preliminary Report on Patentability issued on Jan. 6, 2011 in connection with International Application PCT/US2009/047930, 6 pages.

Kajimoto et al., "Active Tactile Sensor using Deformable Sheet Reflector"Technical Digest of the 16th Sensor Symposium 1998, pp. 99-104.

* cited by examiner

NEW

TACTILE SENSOR USING ELASTOMERIC IMAGING

Matter enclosed in heavy brackets [ ] appears in the original patent but forms no part of this reissue specification; matter printed in italics indicates the additions made by reissue.

PRIORITY INFORMATION

*More than one reissue patent application has been filed for the reissue of U.S. Pat. No. 8,411,140, which include U.S. Reissue patent application Ser. No. 13/971,456, filed Aug. 20, 2013, U.S. Reissue patent application Ser. No. 14/045,668, filed Oct. 3, 2013, U.S. Reissue patent application Ser. No. 14/045,647, filed Oct. 3, 2013, U.S. Reissue patent application Ser. No. 14/045,620, filed Oct. 3, 2013, and U.S. Reissue patent application Ser. No. 14/045,594, filed Oct. 3, 2013.* This application *is a continuation reissue of application Ser. No. 13/971,456, which is an application for reissue of U.S. Pat. No. 8,411,140, and thereby* claims priority from provisional application Ser. No. 61/073,904 filed Jun. 19, 2008, which is incorporated herein by reference in its entirety.

SPONSORSHIP INFORMATION

This invention was made with government support under grant number BCS-0345805 awarded by the National Science Foundation. The government has certain rights in this invention.

BACKGROUND OF THE INVENTION

The invention is related to the field of sensors, and in particular to tactile sensors.

A variety of 2-D tactile tensors have been described in the art. In a typical tensor, an array of individual elements change some electrical property, such as resistance or capacitance, in response to pressure. The electrical changes are sensed and conveyed via wires or other electronic means to the controller or user. Another type of tactile sensor is optical. Some optical property such as luminance or reflectance changes as a result of pressure, and a light sensing system detects and conveys the signal to the controller or user.

For an application such as a robot fingerpad, there are a number of properties that are desired in a tactile sensor. It should have high resolution (be able to make fine spatial discriminations), have high sensitivity (be able to detect small variations in pressure), and be compliant (able to elastically deform in response to pressure). The tactile sensor should be manufacturable with reasonably large areas. It should be easily manufactured using inexpensive materials. It has been impossible to achieve all of these goals in a single sensor.

SUMMARY OF THE INVENTION

According to one aspect of the invention, there is provided a tactile sensor including a photosensing structure, a volume of elastomer that is capable of transmitting an image, and a reflective skin covering the volume of elastomer. The reflective skin is illuminated through the volume of elastomer by one or more light sources, and has particles that reflect light incident on the reflective skin from within the volume of elastomer. The reflective skin is geometrically altered in response to pressure applied by an entity touching the reflective skin, the geometrical alteration causing localized changes in the surface normal of the skin and associated localized changes in the amount of light reflected from the reflective skin in the direction of the photosensing structure. The photosensing structure is positioned to receive a portion of the reflected light in the form of an image, the image indicating one or more features of the entity producing the pressure.

According to another aspect of the invention, there is a method of performing tactile sensing. The method includes providing a volume of elastomer capable of transmitting an image, and covering the volume of elastomer with a reflective skin. The reflective skin is illuminated through the volume of elastomer by one or more light sources, and has particles that reflect light incident on the reflective skin from within the volume of elastomer. The method also includes geometrically altering the reflective skin in response to pressure applied by an entity touching the reflective skin, the alteration causing localized changes in the surface normal of the skin and associated localized changes in the amount of light reflected from the reflective skin in the direction of a photosensing structure. The photosensing structure is positioned to receive a portion of the reflected light in the form an image, the image indicating one or more features of the entity producing the pressure.

DETAILED DESCRIPTION OF THE INVENTION

The invention provides a new approach to making tactile sensors that attain high sensitivity, high spatial resolution, and low cost. In addition, it can be built in a compliant form, so that a robot finger incorporating this sensor can deform elastically in depth, following the profile of the object being manipulated, thereby allowing good control.

Figure 1:
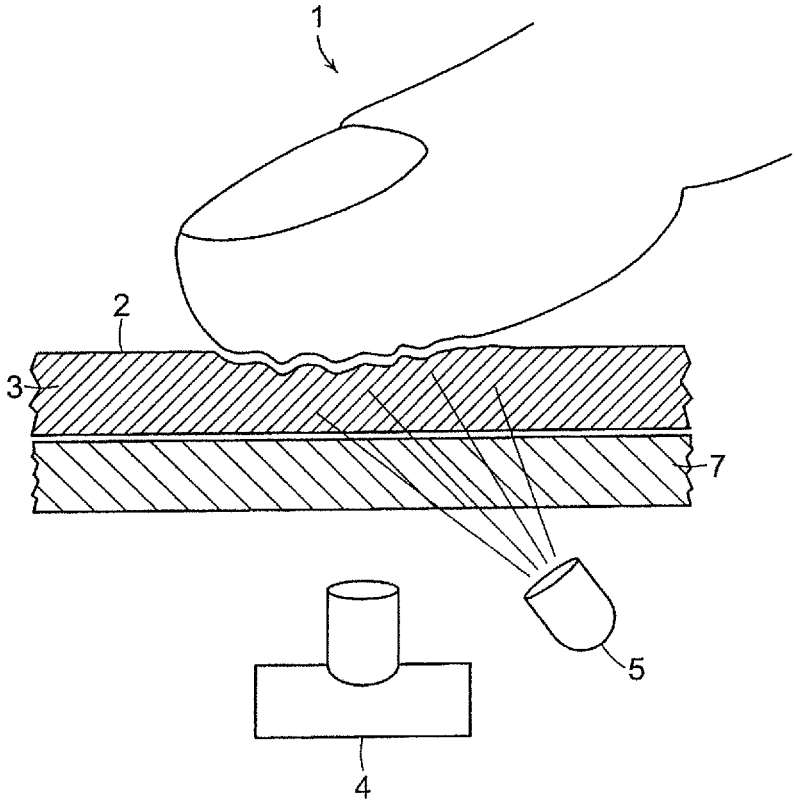
FIG. 1 is a schematic diagram illustrating the elements of a sensor comprising a clear elastomer, a reflective skin, a light source, and a camera in accordance with the invention.

An exemplary embodiment of the invention, as shown in FIG. 1, is made from slab of clear elastomer, 3, supported by a rigid sheet 7 made of glass or other rigid clear material. The surface of the elastomer is coated with a reflective layer 2, referred to as the "skin," which is made, for example, from an elastomeric paint comprising metallic powder embedded in an elastomeric material. The skin has an inner surface (facing the elastomer) and an outer surface (facing the outside world). Light from an illuminator 5 passes through the rigid support 7 and the clear elastomer 3 and strikes the reflective skin 2. When an object such as a finger 1 applies pressure to the outer surface of the skin, it causes a distortion of the skin. Local variations in pressure lead to local variations in the skin's surface normal. A change in the surface normal leads to a change in the amount of light reflected in a given direction. A camera 4 views the inner skin and records the reflected light as an image. The image pattern is the result of the pressure pattern, and thus conveys information about the pressure pattern. Note that the image pixel values do not directly encode pressure. They encode the angle of surface normal, which is indicative of the spatial variation of the pressure.

The clear elastomer can be composed of a wide range of materials including but not limited to silicone rubber, polyurethane, thermoplastic elastomer, plastisol, natural rubber, polyisoprene, polyvinyl chloride, or a mixture thereof. Typically, the hardness of the elastomer, as measured on the Shore A scale, will range between 5 and 90. The reflective skin is also elastomeric, and will typically have a hardness that is equal to or greater than that of the clear elastomer body. The reflective skin may be comprised of the same material as the body, or of a different material.

*The sensor skin can be made by adding reflective particles to the elastomer when it is in a liquid state, via solvent or heat, or before curing. This makes a reflective paint that can be attached to the surface by standard coating techniques such as spraying or dipping. The skin may be coated directly on the surface of the bulk elastomer, or it may be first painted on a smooth medium such as glass and then transferred to the surface of the bulk material and bound there. Also, the particles (without binder) can be rubbed into the surface of the bulk elastomer, and then bound to the elastomer by heat or with a thin coat of material overlaid on the surface. Also, it may be possible to evaporate, precipitate, sputter, other otherwise attach thin films to the surface.*

The reflective particles in the skin may reflect light directionally or non-directionally. If the particles reflect light uniformly in all directions regardless of the light's angle of incidence, the resulting skin will behave like a Lambertian surface, which is entirely non-directional. Titanium dioxide powder, as is used in white paint, leads to a largely Lambertian reflectance. If the reflective particles are comprised of fine metal flakes, and if these flakes tend to be aligned with each other, then the skin will reflect light directionally, meaning that, for a given angle of incident light, there will be a non-uniform distribution of reflected light. If the metal flakes are flat and mirror-like, and if they are well aligned with each other, the distribution of reflected light will be highly directional. If the metal flakes are rough or irregular, or if there is randomness in their alignment, then the distribution of reflected light will be moderately directional, with an appearance resembling sandblasted metal. Directional reflectance can also be obtained with flakes of other materials such as mica. In addition there are pigments comprising flakes covered with multilayer interference coatings that can have different directionality for different wavelengths of light.

*Further still, metal flake powder of aluminum can be used.*

Skin with highly directional reflectance illuminated by a highly directional light source yields a device that is sensitive to small variations in pressure. This sensitivity can be increased by recording the skin's image in its resting state, and using this as a baseline image that is subtracted from images recorded when pressure is applied to the skin. Softer elastomers lead to devices that are more sensitive to low amplitude pressure patterns.

Figure 2:
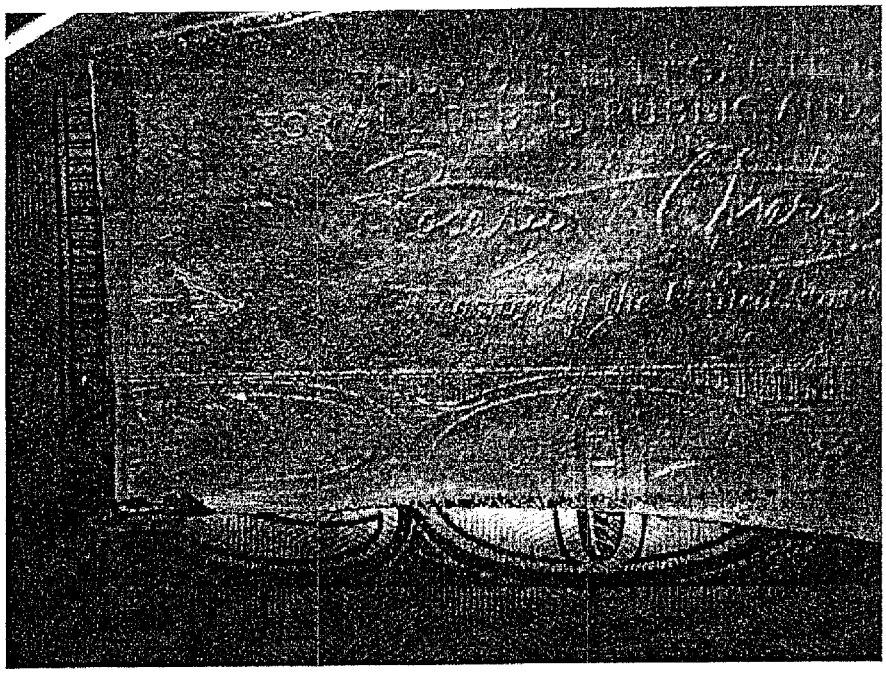
FIG. 2 is a photograph illustrating a slab of a clear elastomer covered with a skin containing fine gold-colored flakes, pressed against a twenty dollar bill.

FIG. 2 shows an image obtained with a skin containing gold-colored bronze flakes that are directionally selective. A slab of a clear elastomer about 1 cm thick, was mounted on a sheet of glass. The slab was coated with a thin skin containing fine gold-colored flakes. The slab was pressed against a twenty dollar bill, and the skin was viewed through the glass and the elastomer. Due to the way that bills are printed, the printing on a twenty dollar bill has a raised relief. When the skin is pressed against the bill, its surface deforms in accordance with the bill's relief. The deformation causes a variation in the amount of light reflected toward the camera, revealing the fine details of the bill's surface in the form of an image.

Figure 3:
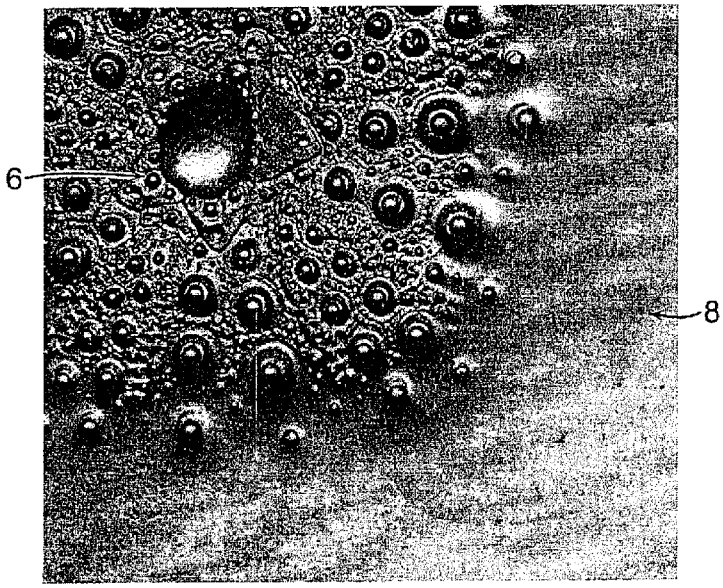
FIG. 3 is a photograph illustrating a slab of a clear elastomer covered with a skin containing fine gold-colored flakes, pressed against a sea urchin shell.

Another example is shown in FIG. 3. A slab of clear elastomer was coated with a reflective skin made with bronze flakes and was placed, skin side up, on the platen of a flatbed scanner. A sea urchin shell was pressed against the reflective skin, causing 3D deformation in the contact region 6. The untouched region 8 remained smooth and the image of this region retained its original smooth appearance. The scanner's internal light source was reflected differently depending on the reflective skin's surface normal, resulting in an image that is recognizable as a shaded relief of the sea urchin shell.

The image pixel values do not directly encode pressure. If spatially uniform pressure is applied to the entire skin surface, there will be no change in surface normal and thus no observable variation in the image. The image pixel values depend on surface normal, which in turn depends on the spatial derivative of pressure. Thus, it is the pattern of pressure variation across the surface that is encoded in the image.

Pressure can be applied to the skin by a rigid object or a non-rigid object. In the case of a non-rigid object, such as a fingertip, both the object and the skin will deform, and the skin's shape will depend on the balance of pressures that the skin and the object exert on each other. Pressure can also be applied by a liquid or gas. For example, a stream of water striking the skin causes it to deform, and the pattern of deformation is visible in the image. If the skin and the elastomer are made of very soft gel-like materials, and if a froth of soap bubbles is placed in contact with the skin, one can visualize the forces exerted by the soap bubble walls.

FIGS. 4A-4D show the elements of the imaging system that can be used in a compact structure such as a robot fingertip. In the illustrated embodiment, there is a rounded piece of elastomer, which is mounted on a rigid member.

Figure 4B:
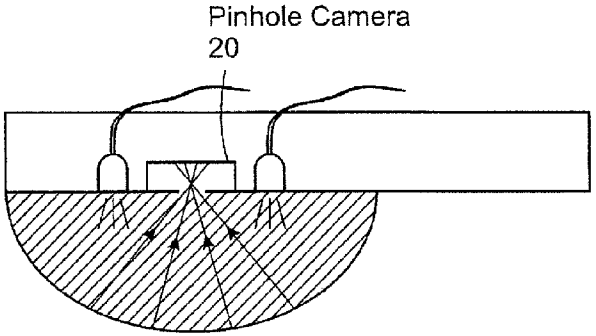
FIGS. 4A-4D are schematic diagrams illustrating the elements of an imaging system that can be used in a compact structure.
Figure 4D:
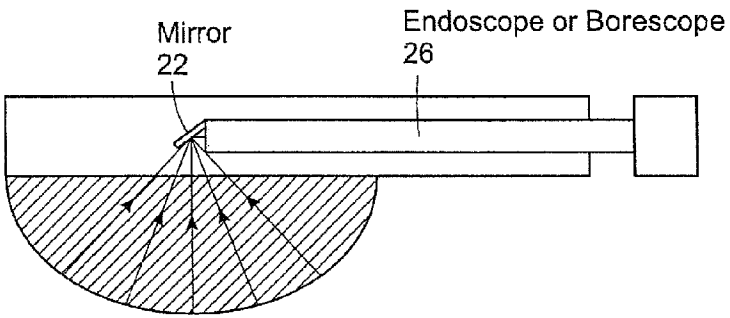
Figure 4A:
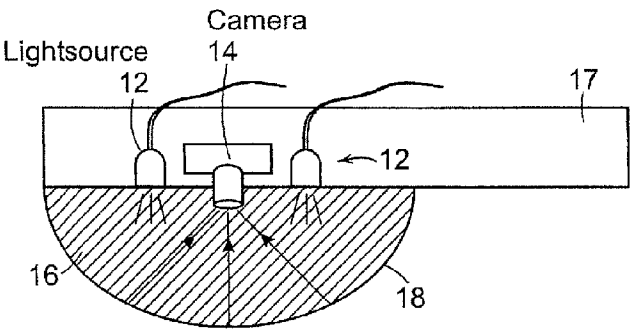
Figure 4C:
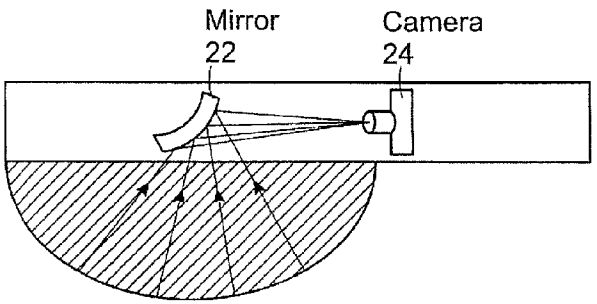

FIG. 4A shows a pair of LEDs 12 and a small camera 14, which are looking through the rounded piece of elastomer 16 positioned on a rigid support 17. The skin 18 of the elastomer is reflective, and the camera forms an image of the inner side of the skin. FIG. 4B shows an example wherein the camera is a pinhole camera 20. FIG. 4C shows a folded path optical system that utilizes a curved mirror 22 which reflects light from the skin to the camera 24. FIG. 4D shows the case where the skin is imaged with an endoscope 26 (or the related videoscope, borescope, fiberscope, or the like). This allows the camera 28 to be placed at a distance from the sensor.

Figure 5A:
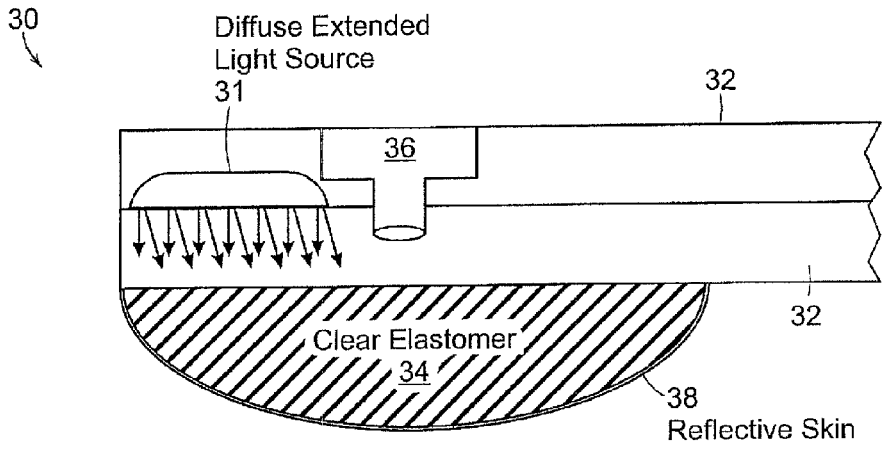
FIGS. 5A and 5B are schematic diagrams illustrating the elements of an imaging system using diffused light and edge illumination in accordance with the invention.

FIG. 5A shows an exemplary embodiment of a sensor 30 using an extended diffuse source of light 31. The diffuse light source 31 and camera 36 are positioned on a rigid support 32. A volume of clear elastomer 34 is positioned on the rigid support 32.

Figure 5B:
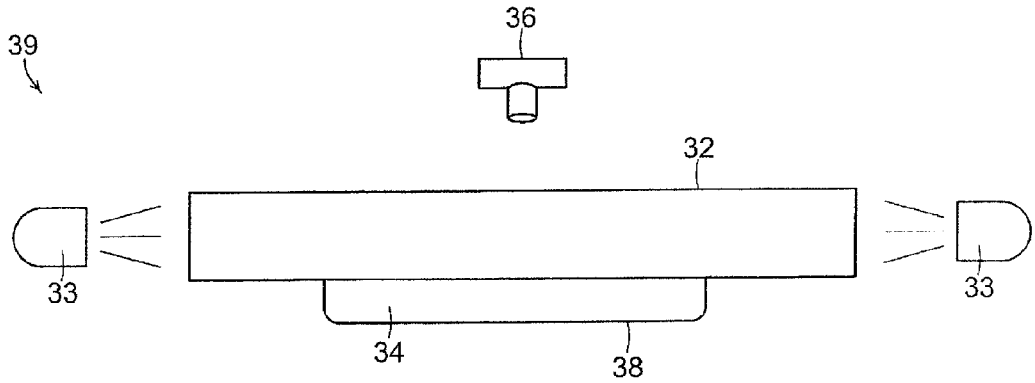

To make the structure compact, it may be preferable to introduce the light at the edge of the support. FIG. 5B shows another exemplary embodiment of the invention where one or more light sources 33 illuminates the sensor from a side or edge of the support 32, preferably made of glass or other clear material. Light will bounce off the back face of the support by total internal reflection, and will also be reflected by the reflective skin surface 38 by ordinary reflection. This will cause many of the light rays to remain within the glass+ elastomer volume; these rays will illuminate the reflective skin surface 38, and the surface can be viewed by the camera 36. It may be advantageous to use a glass wedge rather than an ordinary sheet of glass. With a wedge (for example, the "Light Wedge" book light) the light reflects off the front and back faces successively, making a larger angle with each bounce. This causes a greater amount of light to exit the wedge at larger distance from the light source.

Figure 6B:
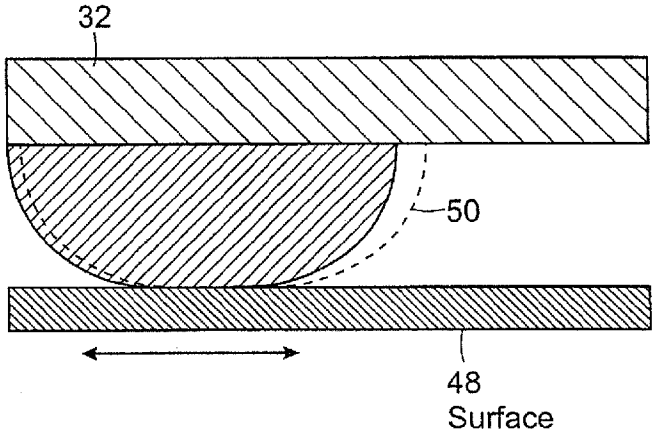
FIGS. 6A-6B are schematic diagrams illustrating the technique used in accordance with the invention to measure deformation and shear.
Figure 6A:
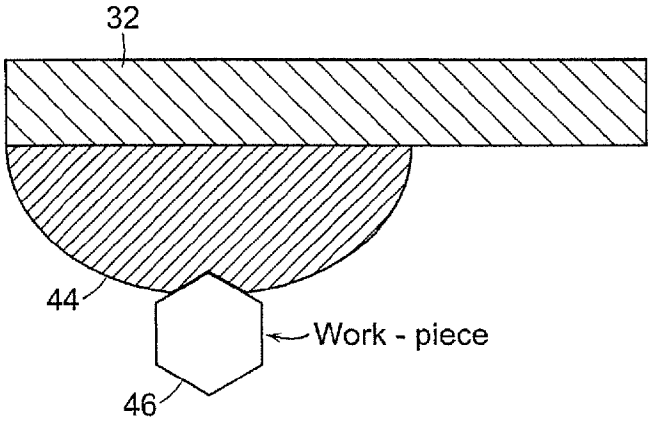

FIGS. 6A-6B show two exemplary embodiments of the invention wherein deformation and shear can be sensed. Deformation (in particular, changes in surface normal) can be sensed by measuring the change in intensity at each point on the skin 44 produced by a work piece 46, as shown in FIG. 6A. FIG. 6B shows a case in which the surface 48 exerts shear forces on the elastomer and skin 50, causing no change in surface normal, but causing a lateral displacement. The skin typically contains a visible microtexture due to the random pattern of reflective particles, and shear causes a displacement of this microtexture. Motion analysis methods can then be used to estimate the shear.

Figure 7A:
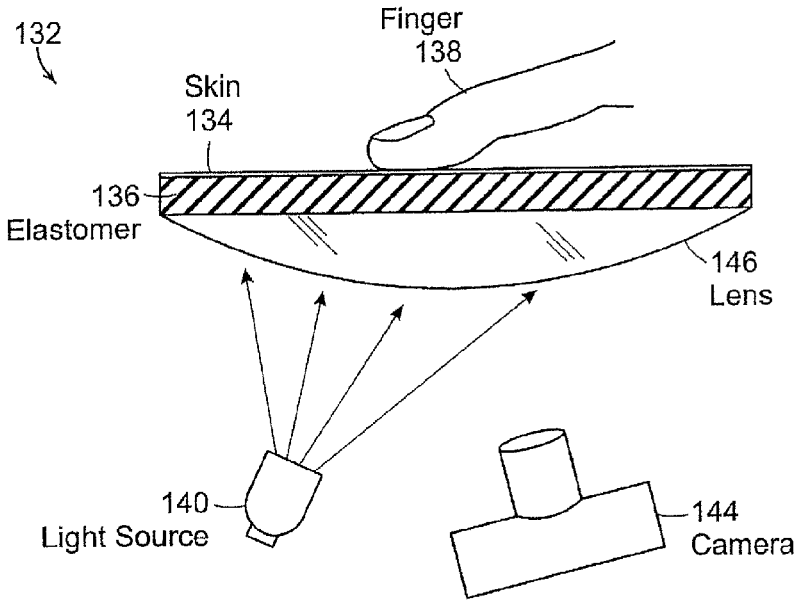
FIGS. 7A and 7B are schematic diagrams illustrating the various tactile sensor arrangements used in accordance with the invention.

In some applications it is desirable that the light source and the camera be placed at optical infinity so that the angle of incidence and reflectance are parallel when the device is in its resting state. This causes the devices optical properties to be spatially uniform across the recorded image. FIG. 7A shows a slab of elastomer 136 covered with reflective skin 134 and mounted on lens 146. An object 138 applies pressure to skin 134. The focal length of the lens is such that the light rays from light source 140 are refracted to be parallel when striking skin 134. Camera 144 views the skin through the same lens. The optical properties of the skin 134 as observed by camera 144 will be fairly uniform across the image.

Figure 7B:
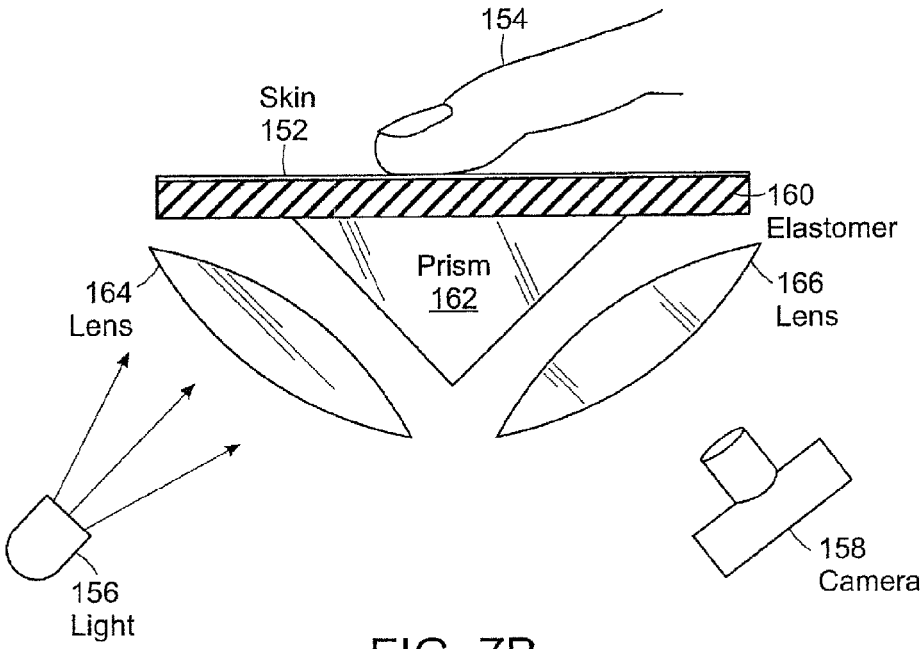

FIG. 7B shows an arrangement in which a slab of elastomer 160 is covered by a reflective skin 152. The elastomer is mounted on a right angle prism 162. Light source 156 passes through lens 164, emerging as parallel rays that enter prism 162 and strike skin 152. An object 154 presses on the skin 152, causing local variation in surface normal. Camera 158 views the skin through a lens 166 that places the skin at optical infinity for that camera. The optical properties of the skin as observed by the camera will be fairly uniform across the image.

Figure 8:
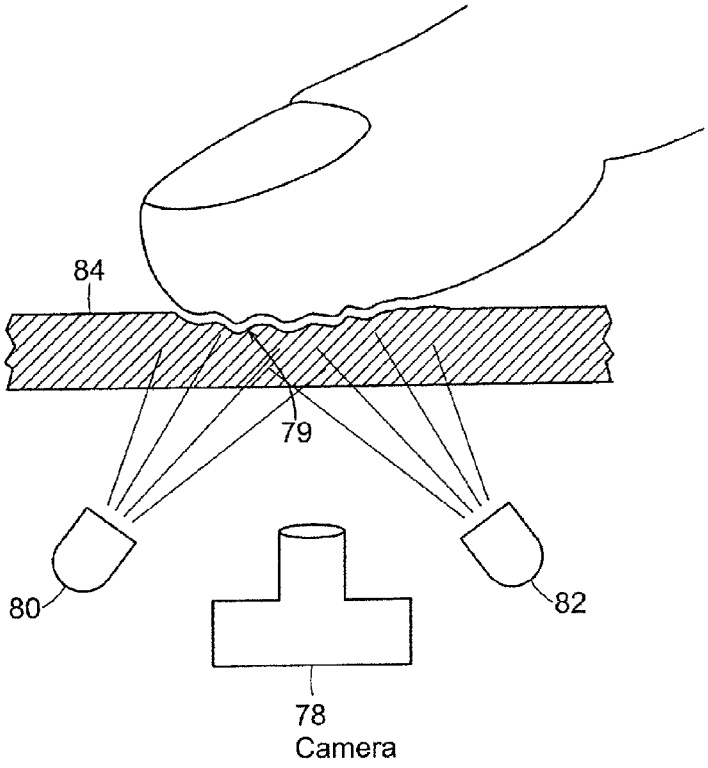
FIG. 8 is a schematic diagram illustrating a structure to reconstruct 3D shape of an object.

In accordance with another exemplary embodiment of the invention, it is desirable to reconstruct the 3-D shape of the deformed surface. In FIG. 8, there are two light sources, 80 and 82, which illuminate the skin 84 thought the elastomer 79. Preferably, the two light sources illuminate the surface from substantially different azimuths, for example one aligned with the x-axis and the other with the y-axis of the slab. The light sources are turned on one after the other and two images are recorded by camera 78. These two images can then be analyzed in accord with the known methods of photometric stereo to estimate the surface normal and surface height at every position. If the two lights 80 and 82 are of different colors, for example red and blue, and if the camera 78 is a color camera, then it is possible to record the two images at the same time in separate color channels. Photometric stereo benefits from the use of additional images. With a color camera it is straightforward to use three light sources and to separate the channels into three images. Alternately, one can use an arbitrary number of light sources if they are turned on one at a time.

The use of multiple lights to get multiple images is useful even when 3D reconstruction is not being performed. Each light brings out surface normal variation along one axis, but not along the orthogonal axis. By using two or more lights, the lights can be arranged so that one light reveals the relief that is missed by another light. This makes it possible to distinguish a wide range of surface normals in different directions. The preferred method of using two or more lights is to have them be different colors, so that a color camera will separate the information about the different lights into different color channels.

*It is also possible to use standard stereoscopic techniques as well, in which multiple cameras are placed in different azimuths relative to the skin of the sensor. The techniques set forth herein of sensing changes in luminance are believed to yield better sensitivity and resolution in many applications relative to known techniques. Furthermore, stereopsis can be used in combination with the techniques disclosed herein. The microtexture of the skin and/or the deformation image can be used to establish correspondence.*

Figure 9:
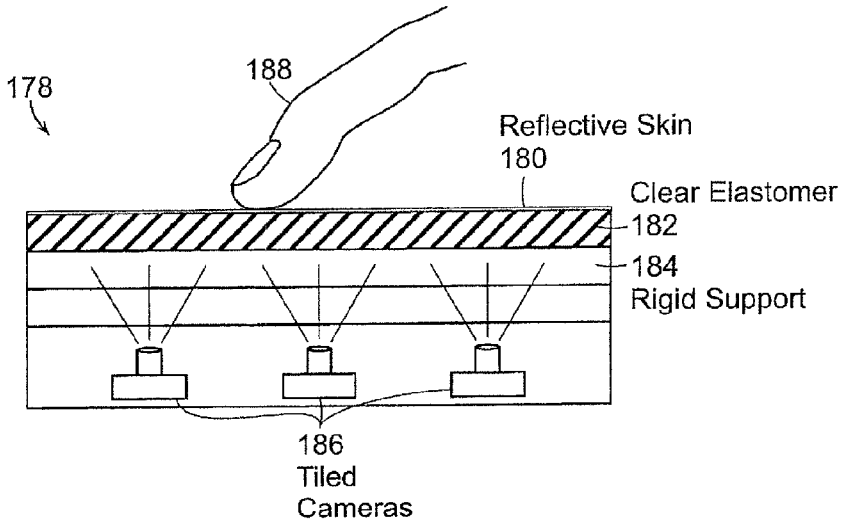
FIG. 9 is a schematic diagram illustrating a large area high resolution sensor formed by tiling a set of smaller sensors.

In some applications it is desirable to make a sensor surface that covers a large area. For example one may require a touchpad that covers an entire desktop. If the device is simply scaled up, then the camera must be placed at a large distance from the surface, making the device undesirably large. One way to ameliorate this problem is to use the methods of folded optics that are used, for example, in many rear projection televisions. Another way is to use a tiled array of cameras, as shown in FIG. 9. The reflective skin 180 covers the clear elastomer 182 which is mounted on a rigid transparent support 184. An array of cameras 186 is placed a short distance from the elastomer and skin. The cameras can be arranged so that their image slightly overlap, and these images can be combined into a single large image by standard stitching techniques.

*In another embodiment, a sensor is formed into a cylinder, which can be rolled over the surface of the object. In one illustrative configuration, the sensor would look like a brayer or paint roller. As the roller rolls over the surface, a video camera inside the roller is aimed continuously at the portion that is in contact with the surface of the object. The series of images so obtained can be combined into a single image by the same methods that are used to obtain panoramic photographs from a series of smaller photographs.*

Figure 13:
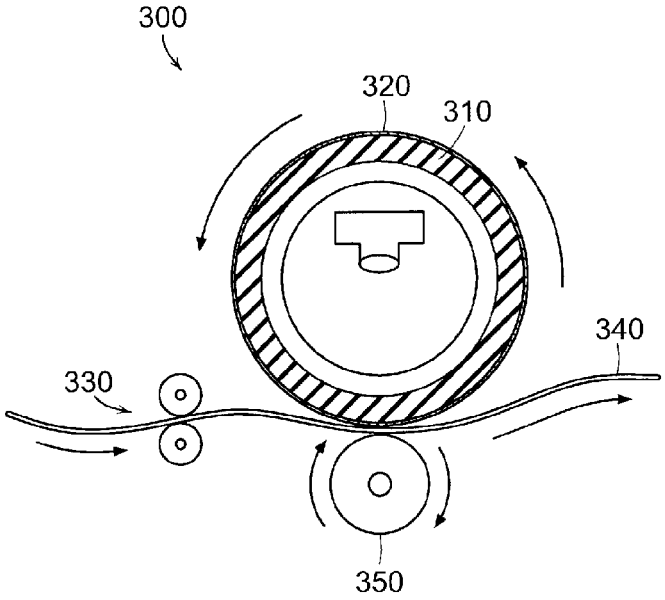
*FIG. 13 is a schematic diagram illustrating the elements of a rolling scanner.*

*Alternatively, the roller could be in a fixed position while the surface of interest was pulled over it. For example, as shown in FIG. 13, an illustrative embodiment of a rolling scanner is a counterfeit banknote detector 300 which has a clear elastomer 310 formed into a cylinder, and a reflective skin 320. The detector 300 also has a slot 330 for feeding a banknote 340. A roller 350, driven by a motor, pulls in the banknote 340 and forms an image of the banknote's surface shape based on an embossed surface of the banknote's paper and/or the raised level of printed ink. A genuine banknote will have a known profile, and a mismatch would indicate a counterfeit banknote.*

In some applications it is advantageous for the skin to have a texture rather than being smooth. In some situations one wishes to study the distribution of pressures across a region of human skin. For example, when a skin care product is applied to the skin, the application process produces a certain distribution of pressure on the skin which changes over time. In order to estimate this changing distribution, a sensor can be made that mimics the texture, elasticity, and other properties of human skin. When a skin care product is, for example, wiped across the artificial skin, it causes the skin to distort in a manner similar to that of human skin. The pattern of distortion can be assessed by making a tactile sensor with mechanical properties emulating human skin. This means that the reflective skin has texture and elasticity like the upper layer of human skin, and the clear elastomer beneath the skin has mechanical properties like the deeper layers of human skin. Multiple layers of clear elastomer with different mechanical properties are required to mimic the complex properties of human skin. When a skin care product is applied to this device, the reflective skin distorts in response to the mechanical forces applied to it, and this distortion is viewed by a camera looking through the clear elastomer layers.

In some applications it may be desired to study the distribution of pressure over the surface of a specific object, such as a tire or the sole of a shoe. It is possible to form the tactile sensor into the same shape as this specific object, and with the same hardness or other mechanical properties as this specific object.

Figure 10:
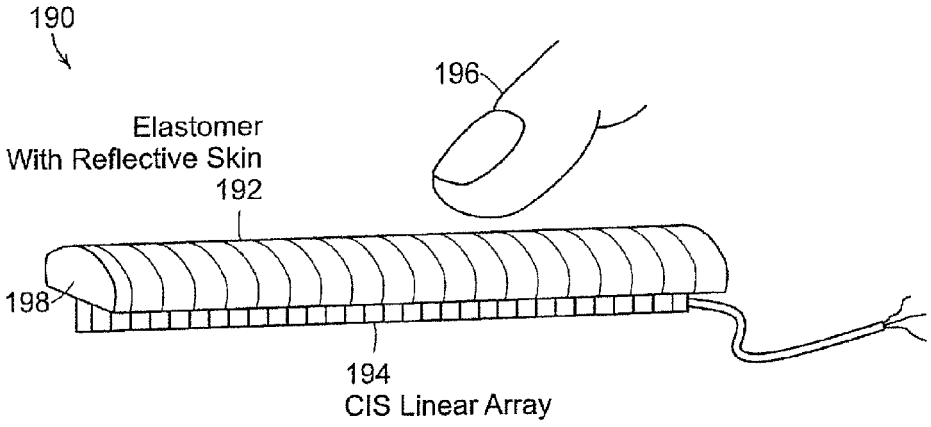
FIG. 10 is a schematic diagram illustrating a contact image sensor (CIS) linear array being used directly in a tactile sensor structure in accordance with the invention.

In other embodiments, it is not necessary that the image be formed by a camera. Many flatbed scanners use a Contact Image Sensor, or CIS, which is a linear array of lenses and photosensors placed in close contact with the object being scanned. No image forming lens is required. FIG. 10 shows a strip of elastomer 198 covered with reflective skin 192 and mounted on CIS 194. When object 196 presses on the skin, it modifies the surface normal, which modifies the amount of light that will be reflected toward the photosensing elements in that neighborhood. The result is a 1D image that encodes information about the location and amplitude of the pressure variation on the skin.

In another embodiment, a multitouch touchscreen device is made in conjunction with a flat panel LED display. A thin sheet of clear elastomer, covered with a semi-reflective skin, covers the front surface of the display. Most of the light that is emitted by the LED's passes through the skin and is seen by a viewer. A portion of the light is reflected by the skin back toward the LEDs. LEDs have the ability to act as photosensors, and thus can be used to measure the amount of reflected light. Pressure variation on the skin causes local changes in the surface normal, which changes the amount of light reflected toward any given LED in the array. The LED photosensing responses comprise an image that is indicative of the pattern of pressure on the skin. This image indicates where the user is touching the screen. In addition, because this is an inherently high resolution image, it is possible to detect the fingerprint of the user. This allows each finger of each user to be distinguished.

Figure 11:
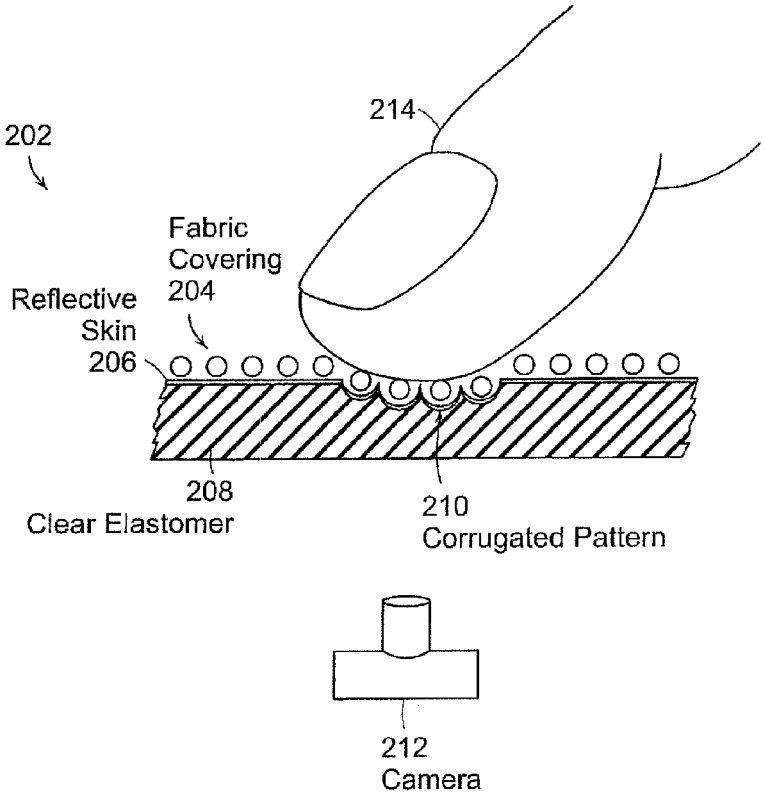
FIG. 11 is a schematic diagram illustrating a fabric covering on the reflective skin.

FIG. 11 shows another exemplary embodiment of a tactile sensor 202 in accordance with the invention. A stretchy fabric is placed over the reflective skin. For some applications such a robot manipulator this fabric will produce a surface with desirable mechanical qualities, including the frictional qualities and the ability to withstand the forces of industrial usage. FIG. 11 shows a cross section of a fabric covering 204 that is attached to the reflective skin 206 on the clear elastomer 208. An object 214 presses on the fabric causing the skin to take on the texture 210 of the fabric. In the case of a woven fabric this pattern appears as a gridwork of fibers corresponding to the fabric's construction. Greater pressure leads to a higher contrast fabric pattern, as seen by camera 212. Local properties of this pattern, including the mean value and the contrast, are indicative of the pressure applied at that location.

Figure 12:
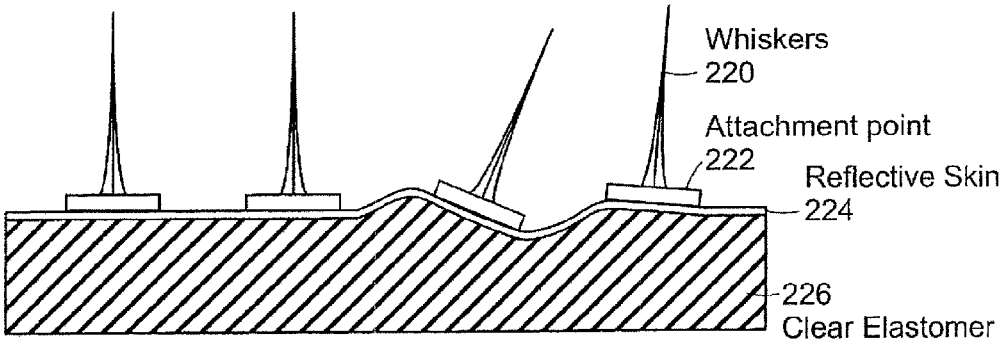
FIG. 12 is a schematic diagram illustrating the use hair or whiskers on the inventive tactile sensor structure.

In another exemplary embodiment, the device is used to measure fluid flow. FIG. 12 shows hairs or whiskers 220 that are attached to the reflective skin 224 at attachment points 222. The attachment points are small pads that are rigidly attached to the whiskers. When fluid flows across the whiskers, it causes the whiskers to tilt, causing the attachment pads to tilt, causing the reflective skin's surface normal to change. The skin is viewed by a camera, and the variation in surface normal causes a variation in image radiance from point to point. The image indicates the speed and direction of fluid flow across each whisker.

There are applications for which high resolution is not needed and not desirable. An extra layer of elastomer on top of the skin acts as a mechanical lowpass filter. For example, a 1 mm thick layer reduces the resolution to be on the order of 1 mm.

*A fluorescent pigment can be used in the skin, illuminated by Ultraviolet (UV) light or blacklight. If the blacklight comes at a grazing angle, it can readily reveal variations in surface normal. The material will be fairly close to Lambertian. To reduce interreflections, one would select a surface that appears dark to emitted wavelengths. This principle is true with ordinary light as well. If one is using a Lambertian pigment in the skin, it is better for it to be gray than white, to reduce interreflections.*

*Blacklight or UV can be used to illuminate a fluorescent surface, which would then serve as a diffuse source. In some cases, it would be useful to use a single short flash (for instance, recording the instantaneous deformation of an object against the surface) or multiple periodic (strobed) flashes (to capture rapid periodic events or to modulate one frequency down to another frequency.)*

Although the present invention has been shown and described with respect to several preferred embodiments thereof, various changes, omissions and additions to the form and detail thereof, may be made therein, without departing from the spirit and scope of the invention.

What is claimed is:

[1. A tactile sensor comprising:

a photosensing structure;

a volume of elastomer capable of transmitting an image; and a reflective skin covering said volume of elastomer, said reflective skin being illuminated through said volume of elastomer by one or more light sources, said reflective skin having particles that non-directionally reflect light incident on the reflective skin from within the volume of elastomer, said reflective skin being geometrically altered in response to pressure applied by an entity touching said reflective skin, said geometrical alteration causing localized changes in the surface normal of said skin and associated localized changes in the amount of light reflected from said reflective skin in the direction of said photosensing structure; wherein said photosensing structure is positioned to receive a portion of said reflected light in the form of an image, said image indicating one or more features of the entity producing said pressure.]

[2. The tactile sensor of claim 1, wherein said volume of elastomer comprises silicone rubber, polyurethane, plastisol, thermoplastic elastomer, natural rubber, polyisoprene, polyvinyl chloride or a mixture thereof.]

[3. The tactile sensor of claim 1, wherein said volume of elastomer comprises a Shore A hardness between 5 and 90.]

[4. The tactile sensor of claim 1, wherein the volume of elastomer is in the form of a slab.]

[5. The tactile sensor of claim 1, wherein said photosensing structure comprises a camera.]

[6. The tactile sensor of claim 1, wherein said photosensing structure comprises an array of sensing elements.]

[7. The tactile sensor of claim 1, wherein said one or more features comprise roughness of said entity.]

[8. The tactile sensor of claim 1, wherein said one or more features comprise the location, amplitude, or direction of the applied pressure.]

[9. The tactile sensor of claim 1, wherein said one or more features comprise the shape, size, or profile of an object producing said pressure.]

[10. The tactile sensor of claim 1, wherein said one or more features comprise the motion or slip of a surface touching the reflective skin.]

[11. The tactile sensor of claim 1, wherein the sensor has physical properties that are similar to those of human skin.]

[12. The tactile sensor of claim 1, wherein the sensor is formed in the shape of a specified object.]

[13. The tactile sensor of claim 1, wherein the reflective skin is illuminated by two or more light sources of different colors.]

[14. A method of performing tactile sensing, comprising:

(a) providing a volume of elastomer capable of transmitting an image;

(b) covering the elastomer with a reflective skin having an inner surface facing the elastomer and an outer surface, wherein the reflective skin comprises particles that non-directionally reflect light incident on the inner surface from within the volume of elastomer;

(c) illuminating the reflective skin through the volume of elastomer with one or more light sources, wherein at least a portion of the light is reflected by the inner surface of the reflective skin;

(d) contacting the outer surface of the reflective skin with an entity, wherein the contact produces pressure that geometrically alters the reflective skin, wherein the alteration causes localized changes in the inner surface of the reflective skin, and wherein the localized changes in the inner surface of the reflective skin cause associated localized changes in the light reflected from the inner surface of the reflective skin;

(e) positioning a photosensing structure to receive a portion of the light reflected from the inner surface of the reflective skin in the form of an image indicating one or more features of the entity contacting the outer surface of the reflective skin.]

[15. The method of claim 14, wherein said volume of elastomer comprises silicone rubber, polyurethane, plastisol, thermoplastic elastomer, natural robber, polyisoprene, polyvinyl chloride or a mixture thereof.]

[16. The method of claim 14, wherein said volume of elastomer comprises a Shore A hardness between 5 and 90.]

[17. The method of claim 14, wherein the volume of elastomer is in the form of a slab.]

[18. The method of claim 14, wherein said photosensing structure comprises a camera.]

[19. The method of claim 14, wherein said photosensing structure comprises an array of sensing elements.]

[20. The method of claim 14, wherein said one or more features comprise roughness of said entity.]

[21. The method of claim 14, wherein said one or more features comprise the location, amplitude, or direction of the applied pressure.]

[22. The method of claim 14, wherein said one or more features comprise the shape, size, or profile of an object producing said pressure.]

[23. The method of claim 14, wherein said one or more features comprise the motion or slip of a surface touching the reflective skin.]

[24. The method of claim 14, wherein the sensor has physical properties that are similar to those of human skin.]

[25. The method of claim 14, wherein the sensor is formed in the shape of a specified object.]

[26. The method of claim 14, wherein the reflective skin is illuminated by two or more light sources of different colors.]

*27. A method of performing tactile sensing, comprising:*

*providing a roller having an outer surface and an inner space;*

*providing a volume of elastomer capable of transmitting an image disposed on the outer surface of the roller, the volume of elastomer having an inner surface in contact with the outer surface of the roller and a reflective surface, opposite the inner surface, that reflects light incident on the reflective surface from within the volume of elastomer;*

*illuminating the reflective surface through the volume of elastomer with a light source, at least a portion of the light being reflected by the reflective surface;*

*rolling the reflective surface along a surface of an entity, thereby sequentially contacting adjacent portions of the reflective surface with adjacent portions of the entity, the contact producing pressure that geometrically alters the contacted portion of the reflective surface, the alteration causing localized changes in the contacted portion of the reflective surface, and the localized changes in the contacted portion of the reflective surface causing associated localized changes in the light reflected from the contacted portion of the reflective surface; and*

*positioning a photosensing structure inside the inner space of the roller to receive a portion of the light reflected from the reflective surface in the form of a sequence of images resulting from the sequential contact with portions of the entity, each image of the sequence indicating one or more features of the portion of the entity contacting the reflective surface.*

*28. The method of claim 27, further comprising combining the sequence of images into a single image.*

*29. The method of claim 28, wherein the combining includes stitching the sequence of images into a panoramic single image.*

*30. The method of claim 27, the rolling the reflective surface along a surface of an entity comprising holding the roller substantially stationary and moving the entity along the reflective surface.*

*31. The method of claim 27, the rolling the reflective surface along a surface of an entity comprising holding the entity substantially stationary and moving the reflective surface along the entity.*

*32. The method of claim 27, further comprising:*

*providing a drive wheel disposed in proximity to the reflective surface;*

*disposing the entity between the drive wheel and the reflective surface; and*

*rotating the drive wheel to cause the adjacent portions of the entity to pass between the drive wheel and the adjacent portions of the reflective surface, thereby rolling the reflective surface along the surface of the entity.*

*33. The method of claim 27, the reflective surface comprising reflective particles that reflect light substantially uni-*

*formly in all directions, the reflective particles causing the reflective surface to reflect light substantially non-directionally.*

*34. The method of claim 27, the reflective surface comprising flakes that exhibit at least one of surface roughness, irregular shape, and random alignment relative to each other, the flakes causing the reflective surface to reflect light moderately directionally.*

*35. The method of claim 27, the reflective surface comprising flakes that are substantially flat, have a mirror-like surface, and are substantially well aligned relative to each other, the flakes causing the reflective surface to reflect light highly directionally.*

*36. The method of claim 27, the volume of elastomer comprising at least one of silicone rubber, polyurethane, plastisol, thermoplastic elastomer, natural rubber, polyisoprene, polyvinyl chloride.*

*37. The method of claim 27, the volume of elastomer comprising a Shore A hardness between 5 and 90.*

*38. The method of claim 27, the photosensing structure comprising a camera.*

*39. The method of claim 27, the photosensing structure comprising an array of sensing elements.*

*40. The method of claim 27, the one or more features comprising roughness of the entity.*

*41. The method of claim 27, the one or more features comprising the location, amplitude, or direction of the applied pressure.*

*42. The method of claim 27, the one or more features comprising at least one of the shape, size, and profile of the entity producing the pressure.*

*43. The method of claim 27, the reflective surface being illuminated by at least two light sources of different colors.*

*44. A sensor comprising:*

*a roller having an outer surface and an inner space;*

*a photosensing structure disposed inside the inner space of the roller;*

*a volume of elastomer capable of transmitting an image disposed on the outer surface of the roller;*

*the volume of elastomer having a reflective surface, the reflective surface reflecting light incident on the reflective surface from within the volume of elastomer, the reflective surface being geometrically altered in response to pressure applied by an entity touching the reflective surface, the geometrical alteration causing localized changes in the surface normal of the reflective surface and associated localized changes in the amount of light reflected from the reflective surface in the direction of the photosensing structure, and*

*the photosensing structure being positioned to receive a portion of the reflected light in the form of an image, the image indicating one or more features of the entity producing the pressure.*

*45. The sensor of claim 44, further comprising a drive wheel disposed in proximity to the reflective surface, the drive wheel positioned such that rotation of the drive wheel causes the entity to pass between the drive wheel and a portion of the reflective surface, thereby causing the roller to rotate and causing adjacent portions of the reflective surface to sequentially contact adjacent portions of the entity.*

*46. The sensor of claim 44, the reflective surface comprising reflective particles that reflect light substantially uniformly in all directions, the reflective particles causing the reflective surface to reflect light substantially non-directionally.*

*47. The sensor of claim 44, the reflective surface comprising flakes that exhibit at least one of surface roughness, irregular shape, and random alignment relative to each other, the flakes causing the reflective surface to reflect light moderately directionally.*

*48. The sensor of claim 44, the reflective surface comprising flakes that are substantially flat, have a mirror-like surface, and are substantially well aligned relative to each other, the flakes causing the reflective surface to reflect light highly directionally.*

*49. The sensor of claim 44, the volume of elastomer comprising at least one of silicone rubber, polyurethane, plastisol, thermoplastic elastomer, natural rubber, polyisoprene, polyvinyl chloride.*

*50. The sensor of claim 44, the volume of elastomer comprising a Shore A hardness between 5 and 90.*

*51. The sensor of claim 44, the photosensing structure comprising a camera.*

*52. The sensor of claim 44, the photosensing structure comprising an array of sensing elements.*

*53. The sensor of claim 44, the one or more features comprising roughness of the entity.*

*54. The sensor of claim 44, the one or more features comprising the location, amplitude, or direction of the applied pressure.*

*55. The sensor of claim 44, the one or more features comprising at least one of the shape, size, and profile of the entity producing the pressure.*

* * * * *